(12) United States Patent
Williams et al.

(10) Patent No.: US 7,435,862 B2
(45) Date of Patent: Oct. 14, 2008

(54) RADIAL REACTOR LOADING OF A DEHYDROGENATION CATALYST

(75) Inventors: David L. Williams, Louisville, KY (US); Andrzej Rokicki, Mountain Lakes, NJ (US); Dennis J. Smith, Louisville, KY (US); Kyle Mankin, Prospect, KY (US)

(73) Assignee: Sud-Chemie Inc., Louisville, KY (US)

( * ) Notice: Subject to any disclaimer, the term of this patent is extended or adjusted under 35 U.S.C. 154(b) by 310 days.

(21) Appl. No.: 11/291,323

(22) Filed: Dec. 1, 2005

(65) Prior Publication Data

US 2006/0142628 A1    Jun. 29, 2006

Related U.S. Application Data

(63) Continuation-in-part of application No. 10/041,422, filed on Jan. 8, 2002, now abandoned, which is a continuation-in-part of application No. 09/923,658, filed on Aug. 7, 2001, now abandoned, which is a continuation-in-part of application No. 09/727,036, filed on Nov. 30, 2000, now abandoned.

(51) Int. Cl.
    *C07C 5/367* (2006.01)
(52) U.S. Cl. ........................... 585/441; 585/444
(58) Field of Classification Search ............. 585/441, 585/444
    See application file for complete search history.

(56) References Cited

U.S. PATENT DOCUMENTS

| | | |
|---|---|---|
| 2,866,790 A | 12/1958 | Pitzer |
| 2,866,791 A | 12/1958 | Pitzer |
| 3,475,508 A | 10/1969 | King |
| 3,515,763 A | 6/1970 | Vitti |
| 3,620,685 A | 11/1971 | Rogers et al. |
| 3,898,049 A | 8/1975 | Burroughs et al. |
| 3,918,918 A | 11/1975 | Kohn et al. |
| 4,039,601 A | 8/1977 | Soderquist et al. |
| 4,372,920 A | 2/1983 | Zardi |
| 4,405,562 A | 9/1983 | Zardi et al. |
| 4,551,571 A * | 11/1985 | Sarumaru et al. ........... 585/440 |
| 4,677,237 A * | 6/1987 | Imai et al. .................... 585/444 |

(Continued)

FOREIGN PATENT DOCUMENTS

EP           532325  A1       3/1973

(Continued)

OTHER PUBLICATIONS

U.S. Appl. No. 09/727,036, filed Nov. 30, 2000, Williams et al.

(Continued)

*Primary Examiner*—Thuan Dinh Dang
(74) *Attorney, Agent, or Firm*—Joan L. Simunic

(57) ABSTRACT

A radial reactor for utilization for catalytic reactions of gaseous or liquid feedstreams including an annular catalyst bed, wherein the material contained within the catalyst bed includes an active catalyst material, contained within an outer ring-shaped layer of the catalyst bed, and a generally inert material, contained within an inner ring-shaped layer of the catalyst bed, wherein the generally inert material includes a potassium-containing compound, such as potassium oxide, hydroxide, carbonate or bicarbonate.

11 Claims, 2 Drawing Sheets

U.S. PATENT DOCUMENTS

| | | |
|---|---|---|
| 4,755,362 A | 7/1988 | Zardi |
| 4,769,220 A | 9/1988 | Zardi |
| 4,777,319 A | 10/1988 | Kung et al. |
| 4,880,603 A | 11/1989 | Forster |
| 4,904,453 A | 2/1990 | Zardi |
| 4,952,375 A | 8/1990 | Zardi |
| 4,963,338 A | 10/1990 | Zardi et al. |
| 5,006,316 A | 4/1991 | Zardi et al. |
| 5,043,500 A | 8/1991 | Tagamolila |
| 5,250,270 A | 10/1993 | Noe |
| 5,358,698 A | 10/1994 | Butler et al. |
| 5,510,553 A | 4/1996 | Delorme et al. |
| 5,756,048 A | 5/1998 | Zardi et al. |
| 6,069,937 A | 5/2000 | Oshino et al. |
| 6,177,602 B1 | 1/2001 | Williams et al. |
| 6,191,065 B1 | 2/2001 | Williams et al. |
| 6,242,379 B1 | 6/2001 | Williams et al. |

FOREIGN PATENT DOCUMENTS

| | | |
|---|---|---|
| EP | 532325 A1 | 3/1993 |
| EP | 1142631 A1 | 10/2001 |
| GB | 794915 | 5/1958 |
| GB | 794915 | 5/1959 |

OTHER PUBLICATIONS

U.S. Appl. No. 09/923,658, filed Aug. 7, 2001, Williams et al.
U.S. Appl. No. 09/727,036, filed Nov. 30, 2000, Williams et al.

* cited by examiner

RADIAL REACTOR LOADING OF A DEHYDROGENATION CATALYST

CROSS REFERENCE TO RELATED APPLICATIONS

This application is a continuation-in-part of application Ser. No. 10/041,422, filed Jan. 8, 2002 now abandoned, which was a continuation-in-part of application Ser. No. 09/923,658, filed Aug. 7, 2001 now abandoned, which was a continuation-in-part of application Ser. No. 09/727,036, filed on Nov. 30, 2000 now abandoned, all three applications being incorporated herein in their entirety by reference.

BACKGROUND

The present invention is a method for the nonoxidative dehydrogenation of an alkylaromatic feedstream using a radial reactor. The radial reactor comprises a dehydrogenation catalyst bed having a dehydrogenation catalyst material layer and a layer of an inert material containing a potassium compound. The catalyst bed is divided into inner and outer ring-shaped layers, wherein catalyst material is placed in the outer layer and inert material containing a potassium compound is placed in the inner layer.

Radial reactors are known in the art and are utilized for a number of different types of catalytic reactions. For example, radial reactors are commonly utilized for the dehydrogenation of hydrocarbons, such as the dehydrogenation of acyclic and aromatic hydrocarbons to their correspondingly less saturated hydrocarbon products. One of the best known of these dehydrogenation processes is the conversion of ethylbenzene to styrene.

The conventional ethylbenzene dehydrogenation process (referred to as "nonoxidative dehydrogenation") generally uses an iron oxide catalyst and the reaction takes place in the absence of oxygen. The conversion of ethylbenzene to styrene is an endothermic reaction which requires the addition of heat to the process to maintain an appropriate level of activity. In addition, it has been found that regulating the flow rate of the ethylbenzene as it passes across the catalyst bed, regardless of the thickness of the catalyst bed in the reactor assembly, can generally ensure that an acceptable level of selectivity and activity for the reactions is maintained. But even with such regulation the catalyst material will lose selectivity and activity over time.

The commercial process for the conversion of ethylbenzene to styrene is normally conducted in a series of radial, adiabatic reactors. It has been observed that a reactor system containing multiple radial reactors may produce a higher degree of conversion of the hydrocarbon and may have greater product yield than is exhibited by use of a single radial reactor. Thus, it is not uncommon for three or more radial reactors to be arranged in a serial flow orientation with reheat means, which may be located both within and between the reactors, to add heat to the reaction.

Conventional radial reactors contain an inlet located in the center of the radial reactor assembly. Catalysts for the reaction are placed within a bed or beds in the reactor assembly, generally occupying a ring-shaped, vertical space, which is located outside of a central core of the reactor. The feedstream enters the reactor through the inlet and then flows radially outward through the catalyst bed to an open, annular space, which is formed outside of the catalyst bed but within the reactor assembly. Ultimately the feedstream flows to an outlet as shown, for example, in U.S. Pat. No. 3,898,049.

In radial reactors used for ethylbenzene dehydrogenation, the gas feed flows radially from the central core of the reactor assembly through catalyst material contained in a ring-shaped, vertical catalyst bed contained within the radial reactor. However, because the nonoxidative dehydrogenation of ethylbenzene is a temperature sensitive reaction, the volume of the catalyst material within the catalyst bed that actually catalyzes the feedstream is often limited. For example, in nonoxidative dehydrogenation radial reactors for the dehydrogenation of ethylbenzene, only the first 4 inches (10 cm) to 15 inches (40 cm) or so of thickness of the catalyst material contained in the ring-shaped, vertical layer of the catalyst bed effectively dehydrogenates the ethylbenzene feedstream. This section of the catalyst bed also loses the greatest amount of the potassium during the dehydrogenation reaction. Because the reaction is adiabatic, by the time the ethylbenzene feedstream has passed about 18 inches (46 cm) or so through the catalyst bed, the temperature of the feedstream has dropped to such an extent that the activity of the reaction is diminished dramatically or even extinguished. Further, when the temperature of the ethylbenzene feedstream drops as it passes through a thick catalyst bed, a higher percentage of undesired by-products are produced. In addition, the greater the thickness of the catalyst bed, the greater the pressure drop as the feedstream passes through the catalyst bed.

Notwithstanding these reductions in the performance of the catalyst material in the thick catalyst beds contained in large diameter radial reactors, it has become conventional to build shorter reactor assemblies with thicker catalyst beds instead of building taller radial reactors with thinner catalyst beds because of the high cost in building both the support structure for the reactors and the radial reactors themselves. While shorter, thicker radial reactors contain the same overall quantity of catalyst material as taller, thinner radial reactors, the performance of these shorter, thicker reactors is not as efficient as when a taller, but narrower reactor is utilized.

Conventional nonoxidative dehydrogenation processes generally utilize a single dehydrogenation catalyst, such as a conventional iron oxide catalyst containing a small amount of potassium and chrome as disclosed, for example, in U.S. Pat. Nos. 2,866,790 and 2,866,791. Various catalysts for nonoxidative dehydrogenation are also disclosed in U.S. Pat. No. 6,191,065. The teachings of the '790 patent, the '791 patent and the '065 patent are incorporated herein by reference. These conventional catalysts when used for the conversion of ethylbenzene to styrene gradually deactivate during normal use, causing a reduction in ethylbenzene conversion. As part of the deactivation process, the catalyst loses potassium. During the dehydrogenation reaction, potassium migrates across the catalyst bed from the inlet side to the outlet side. Thus, the catalyst located closest to the inlet generally exhibits the greatest potassium loss over time.

Several attempts have been made to address the problem of loss of potassium from the dehydrogenation catalyst during a nonoxidative dehydrogenation reaction. For example, an alkali metal or alkali metal compound can be introduced continuously or intermittently to the reactant stream. Alternatively, the alkali metal compound can be added in the form of a dry solid powder, or a solid lump containing the alkali metal compound can be placed in the path of the heated reactant feedstream causing the lump to gradually vaporize during processing. However, these are generally unsatisfactory fixes for the overall problem of the potassium loss. Thus, there is a need for a more effective means of introducing or maintaining potassium in the catalyst bed for nonoxidative dehydrogenation reactions.

SUMMARY OF THE INVENTION

The present invention is a method for the nonoxidative dehydrogenation of an alkylaromatic feedstream using a radial reactor. The method comprises loading a conventional multilayer catalyst bed radial reactor with a vertical outer layer of a dehydrogenation catalyst material and with a vertical inner layer of an inert material containing a potassium compound. The feedstream is delivered to the radial reactor through an inlet located in the center of the radial reactor assembly. The feedstream then flows radially outward through the vertical inner layer of the catalyst bed and then through the vertical outer layer of the catalyst bed. As the treated feedstream exits the outer layer of the catalyst bed, it is fed into an open space formed between the outermost edge of the vertical outer layer and the inside surface of the exterior reactor wall, and is directed toward the reactor outlet.

In addition, a catalyst system is taught for use in a catalyst bed of a radial reactor, particularly for the dehydrogenation of alkyl aromatics. The catalyst system comprises an iron oxide and potassium oxide dehydrogenation catalyst for loading in the vertical outer layer of the catalyst bed of the radial reactor and a potassium-containing compound selected from the group consisting of potassium oxide, potassium hydroxide, potassium carbonate, potassium bicarbonate, potassium salts and combinations thereof supported on an essentially inert material having a surface area of from about 0.1 $m^2/g$ to about 50 $m^2/g$, such as an alpha alumina or a ceramic material including ceramic monoliths, for loading in the vertical inner layer of the catalyst bed of the radial reactor.

DETAILED DESCRIPTION OF THE PREFERRED EMBODIMENT

The radial reactors depicted in the various Figures are selected solely for the purposes of illustrating the invention. Other and different radial reactors may utilize the inventive features described herein as well and are intended to fall within the scope of this invention, even absent illustration.

Figure 1:
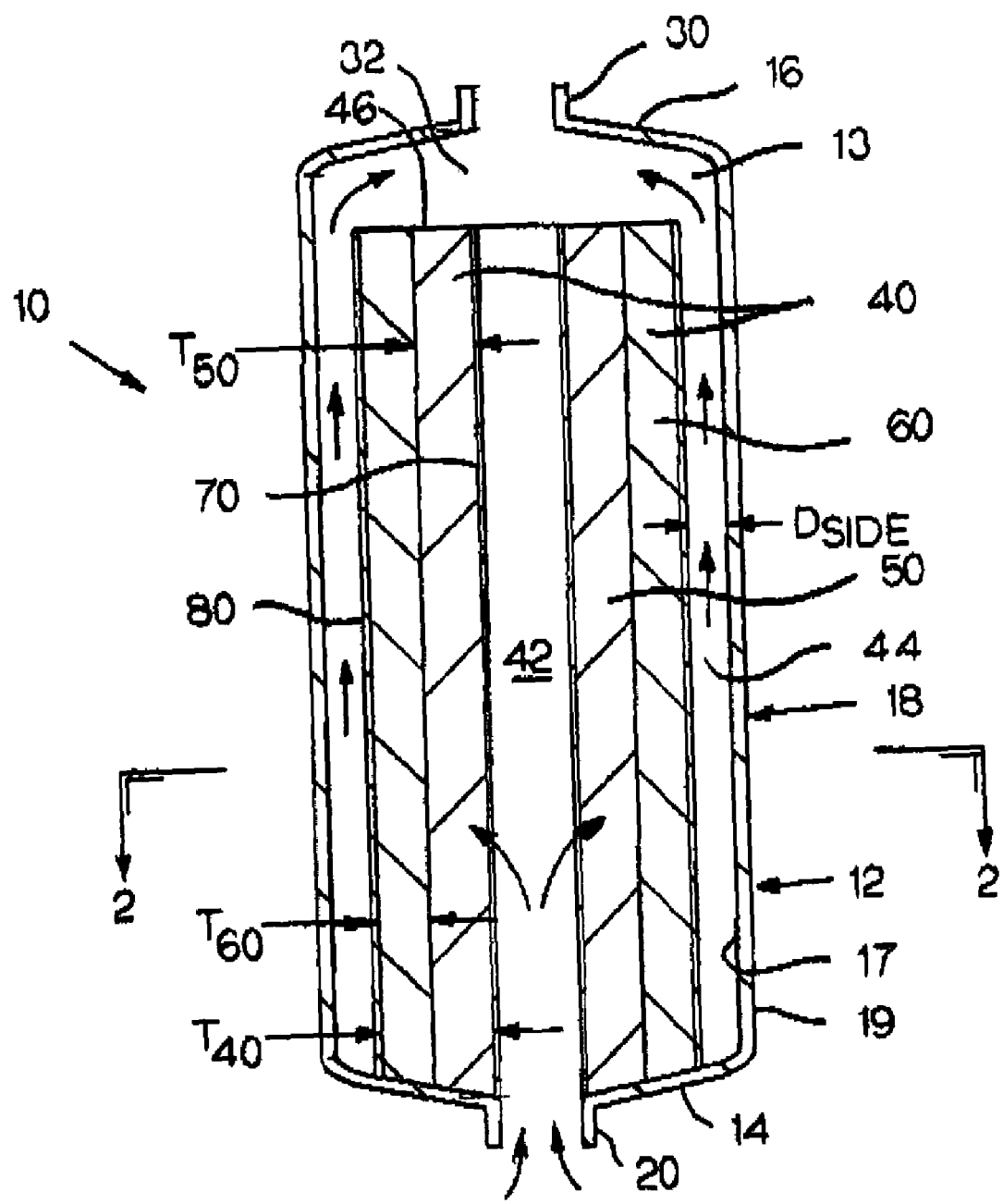
FIG. 1 is a schematic view of a radial reactor of the invention.
Figure 2:
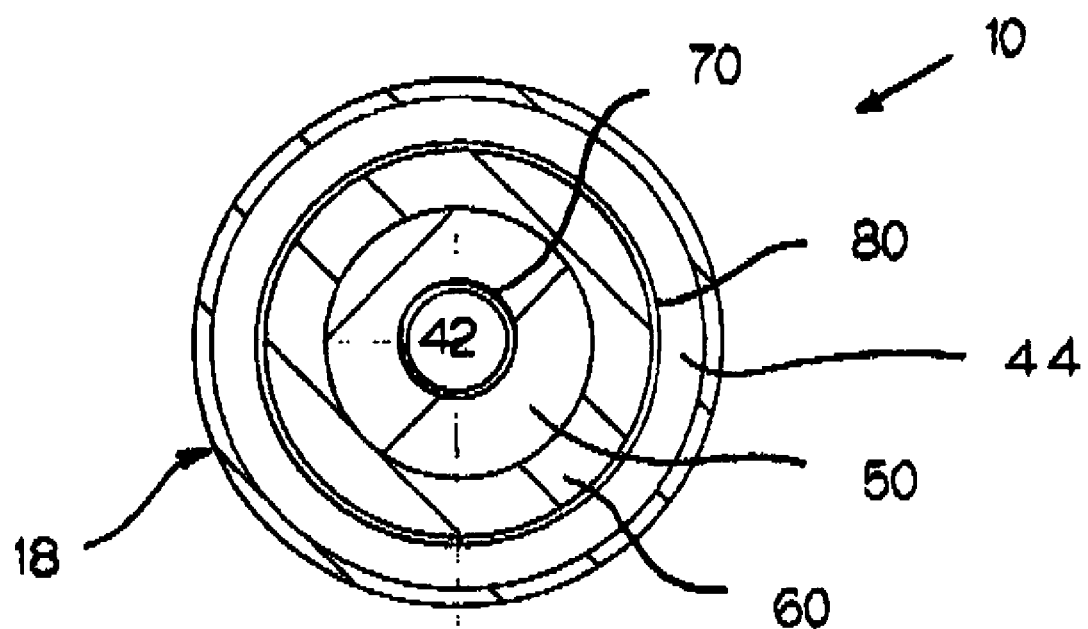
FIG. 2 is a cross-sectional view of the catalyst bed and central core of the radial reactor of FIG. 1 taken along line 2-2.

The present invention is a method for the nonoxidative dehydrogenation of an alkylaromatic feedstream using a conventional radial reactor unit and a catalyst system for use in the method. As shown in FIGS. 1-3, a conventional radial reactor (10) comprises a reactor shell (12) that includes an inlet (20) and an outlet (30) and a catalyst bed (40).

More specifically, the reactor shell (12) has an inlet side (14) and an outlet side (16) and a vertical reactor wall (18) connecting said inlet side (14) to said outlet side (16), and thereby creating an interior cavity (13). The reactor shell (12) defines an interior cavity surface (17) and an external surface (19). The inlet (20) projects through the inlet side (14) to allow a feedstream to be fed into the interior cavity (13). The outlet (30) projects through the outlet side (16) to allow a product stream to exit from the interior cavity (13).

An inner screen (70) and an outer screen (80) are positioned within the interior cavity (13), and are designed to retain the catalyst bed (40). The inner screen (70) is mounted within the interior cavity (13) so as to create a central core (42) surrounded by the catalyst bed (40), which may comprise one or more layers of catalyst materials. The outer screen (80) is mounted within the interior cavity (13) parallel to the vertical reactor wall (18) but separated from the vertical reactor wall (18) by a predetermined distance, "$D_{side}$". The inner screen (70) and outer screen (80) are secured to the interior cavity surface (17) of the inlet side (14) and run from the inlet side (14) essentially parallel to the vertical reactor wall (18) toward the outlet side (16), but terminate before reaching the interior cavity surface (17) of the outlet side (16). When the catalyst bed (40) is loaded between the screens (70, 80) a headspace (32) that is contiguous with the outlet (30) is formed between the top of the catalyst bed and the outlet side (16) of the radial reactor (10), and a channel (44) that is contiguous with the headspace (32) is formed between the outer screen (80) and vertical reactor wall (18). A catalyst bed thickness, $T_{40}$, is defined as the distance between the inner screen (70) and the outer screen (80).

At the top of the catalyst bed near the headspace (32), the catalyst bed has a cap (46). The cap (46) is intended to prevent the allowing the feedstream from entering the reactor (10) at the inlet (20), then flowing straight through the central core (42) and out the outlet (30). Rather, the feedstream is prevented from exiting the central core (42) by the cap (46) and is forced through the catalyst bed (40) and into the channel (44) where the now-treated feedstream, or product stream, flows into the headspace (32) and out the outlet (30).

In a preferred embodiment of the present invention, the catalyst bed (40) comprises at least two vertical layers—a vertical inner layer (50) mounted along the inner screen (70) and closest to the central core (42) and a vertical outer layer (60) mounted between the inner layer (50) and the channel (44). Optionally, a third screen may be mounted between the vertical layers to retain the catalyst materials in their respective layers. Each vertical layer (50, 60) has a predetermined thickness, $T_{50}$ and $T_{60}$, respectively, and the thickness of each layer may vary depending on the application. With the multilayer catalyst bed, as the feedstream is fed into the interior cavity (13) it is forced initially through the vertical inner layer (50) of catalyst material and then through the vertical outer layer (60) of catalyst material before exiting into the channel (44).

The invention, then, is a method for the nonoxidative dehydrogenation of an alkylaromatic feedstream that comprises loading the vertical outer layer (60) with a dehydrogenation catalyst material and loading the vertical inner layer (50) with an inert material containing a potassium compound. A fluid feedstream, gaseous or liquid, comprising ethylene is fed into the radial reactor (10) though inlet (20) and is forced, via pressure, into central core (42). As additional fluid is forced into the reactor (10) through the inlet (20), the fluid in the central core (42) penetrates through the inner screen (70) and migrates through the vertical inner layer (50) with the inert material containing a potassium compound, and then migrates through the vertical outer layer (60) with a dehydrogenation catalyst material. The now-treated fluid then exits the vertical outer layer (60) into the channel (44), then flows into the headspace (32) and exits the reactor through the outlet (30). During the course of the fluid flow, potassium may be lost from the active catalyst material. However, the potassium-containing supported material of the vertical inner layer (50) is designed to release potassium under typical nonoxidative dehydrogenation reaction conditions so the potassium from the vertical inner layer (50) can migrate to the vertical outer layer (60) to replace the potassium lost from the active catalyst material, thereby extending the effective lifetime of the active catalyst material.

More specifically, the dehydrogenation catalyst material is an iron oxide and potassium oxide dehydrogenation catalyst and the inert material containing a potassium compound is a an essentially inert material having a surface area of from about 0.1 m²/g to about 50 m²/g, such as an alpha alumina or a ceramic material including ceramic monoliths, supporting a potassium-containing compound selected from the group consisting of potassium oxide, potassium hydroxide, potassium carbonate, potassium carbonate, potassium salts and combinations thereof.

In an exemplary embodiment of the present invention, the catalyst bed (40) is loaded to effect the nonoxidative dehydrogenation of ethylbenzene to styrene. For this purpose, the vertical outer layer (60) defines a thickness, $T_{60}$, of from about 4 inches to about 48 inches, preferably from about 6 inches to about 36 inches, most preferably from about 18 inches to about 24 inches. The vertical inner layer (50) defines a thickness, $T_{50}$, of the difference between the catalyst bed thickness, $T_{40}$, and the vertical outer layer thickness, $T_{60}$. Because most conventional radial reactors provide for a catalyst bed thickness of from about 4 inches to about 48 inches, the vertical inner layer (50) thickness, $T_{50}$, would be up about to about 44 inches.

Recommended dehydrogenation catalyst materials for the vertical outer layer (60) include, without limitation, any conventional commercial or proprietary dehydrogenation catalyst, such as Styromax®, a catalyst produced by Süd-Chemie Inc. and comprising iron oxide and potassium oxide. In a preferred embodiment, the nonoxidative dehydrogenation catalyst material contained in the outer, ring-shaped, vertical layer (60) is selected from the catalysts disclosed in U.S. Pat. Nos. 6,242,379, 6,191,065 and 6,177,602, which are incorporated herein by reference.

Two or more nonoxidative dehydrogenation catalysts may be utilized together within the active catalyst material layer of the radial reactor (10), each forming a different vertical layer as long as the overall thickness of the layer of the active catalyst material does not dramatically reduce the overall performance of the radial reactor (10). When more than one layer of nonoxidative dehydrogenation catalysts is utilized, preferably at least one of the catalysts has a different performance and/or operating characteristic than at least one of the other catalysts. Different layers of the same catalysts may also be sandwiched around a catalyst with different operating or performance characteristics, depending upon the overall performance or operating characteristics that are desired.

Recommended potassium-containing supported materials for the vertical inner layer (50) include, without limitation, any material which comprises potassium and does not adversely interfere with the catalytic reaction of the catalyst material contained in the catalyst bed (40). That is, the potassium-containing supported materials generally should not react with the components of the feedstream to produce unwanted byproducts, nor adversely impact the physical or chemical characteristics of the catalyst material during reaction, but which may replace a portion or all of the potassium that is lost from the active catalyst material during catalytic activity. Further, the potassium-containing supported materials will preferably be formed in a shape which limits the overall pressure drop through the catalyst bed (40) and which has adequate crush strength. The crush strength is preferably the same as or greater than that of the active catalyst material. The potassium-containing supported materials may be formed in a similar size and shape to the catalytic material to facilitate loading, but the size and shape are not intended to be limited by the size and shape of the active catalyst material.

Recommended supports for the potassium-containing supported materials include, without limitation, an inert material with a surface area from about 0.1 m²/g to about 50 m²/g, preferably from about 1 m²/g to about 20 m²/g, such as an alpha alumina or a ceramic material including ceramic monoliths. The generally inert material that is chosen should be one that can receive and adsorb an appropriate amount of the potassium-containing compound. The amount of the potassium-containing compound that is added to the inert material should be sufficient to replace substantially any potassium that is lost from the dehydrogenation catalyst during conventional processing of the alkylaromatic feedstream over the conventional life of the catalyst bed. The amount of the potassium-containing compound that is added to the inert base material will depend on the composition of the generally inert material and may vary, sometimes dramatically. In an exemplary embodiment, the amount of the potassium-containing component that is added to the inert material comprises, after addition, at least about 0.1 wt %, preferably from about 1 wt % to about 40 wt %, and most preferably from about 5 wt % to about 20 wt % of the inert material. Further, the potassium-containing compound may be loaded into the radial reactor (10) so as to be in excess of any anticipated potassium loss from the active catalyst material. The availability of excess potassium is not expected to be detrimental to the performance of the active catalyst material.

Sources of potassium for the potassium-containing compounds are generally known in the art, and may include potassium oxide, potassium hydroxide, potassium carbonate, potassium bicarbonate, similar potassium salts and compounds, and combinations thereof. Potassium chloride is not generally recommended as any residual chloride ions may adversely affect the catalyst performance, as is known in the art.

By layering the catalyst bed of the radial reactor with an active catalyst material and a material that can provide potassium to supplement for any potassium lost from the active catalyst material during reaction, the life of the catalytic material is lengthened and the overall selectivity and activity of the catalyst material is enhanced for an extended period of time. In addition, in the inventive design, the catalyst material in the vertical outer layer (60) presents a higher surface area for reaction with the feedstream than if only catalyst material is utilized within the catalyst bed (40) because the overall surface area of the catalyst material portion of the catalyst bed (40) is greater the further one moves radially outward from the center (42) of the radial reactor (10). Further, in the inventive design, the volume of the catalyst material which is exposed to the feedstream at the proper operating parameters is optimized, so there is a greater "effective" utilization of the catalyst material, thus resulting in higher performance of the catalyst material within the catalyst bed (40).

It is understood that, in light of a reading of the foregoing description and drawings, those with ordinary skill in the art will be able to make changes and modifications to the present invention without departing from the spirit or scope of the invention, as defined herein. For example, although conventional radial reactors are essentially tube-shaped providing for a circular cross-section, those skilled in the art would be expected to achieve benefits similar to those reported herein from the inclusion of a potassium source with an active catalyst material in a reactor having a cross-section that varies from the circular shape.

What is claimed is:

1. A process for the nonoxidative dehydrogenation of alkylaromatic hydrocarbons to alkenylaromatic hydrocarbons wherein said process comprises loading a radial reactor having a catalyst bed that defines a vertical inner layer and a vertical outer layer with an inert material containing a potassium compound in the vertical inner layer and with a dehydrogenation catalyst material in the vertical outer layer, and then introducing a fluid feedstream of said alkylaromatic hydrocarbons into said radial reactor though an inlet and forcing said fluid feedstream into a central core of said radial reactor, and then through an inner screen, and then through said vertical inner layer, and then through said vertical outer layer, and then through an outer screen, and then into a channel that flows into a headspace and exits said radial reactor through an outlet.

2. The process of claim 1 wherein said dehydrogenation catalyst material is an iron oxide and potassium oxide dehydrogenation catalyst.

3. The process of claim 1 wherein said inert material containing a potassium compound is an essentially inert material having a surface area of from about 0.1 $m^2$/g to about 50 $m^2$/g.

4. The process of claim 3 wherein said inert material containing a potassium compound is an essentially inert material having a surface area of from about 0.1 $m^2$/g to about 20 $m^2$/g.

5. The process of claim 3 wherein said inert material containing a potassium compound having a surface area of from about 0.1 $m^2$/g to about 50 $m^2$/g is alpha alumina or a ceramic material.

6. The process of claim 3 wherein said inert material containing a potassium compound having a surface area of from about 0.1 $m^2$/g to about 50 $m^2$/g supports a potassium-containing compound is selected from the group consisting of potassium oxide, potassium hydroxide, potassium carbonate, potassium carbonate, potassium salts and combinations thereof.

7. The process of claim 1 wherein said inert material containing a potassium compound comprises said potassium compound at a concentration of at least about 0.1 wt % of the inert material.

8. The process of claim 7 wherein said potassium compound has a concentration of from about 5 wt % to about 20 wt % of the inert material.

9. The process of claim 1 wherein said vertical outer layer defines a thickness of from about 4 inches to about 48 inches.

10. The process of claim 9 wherein said vertical outer layer defines a thickness of from about 18 inches to about 24 inches.

11. The process of claim 1 wherein said dehydrogenation catalyst material comprises at least two nonoxidative dehydrogenation catalysts wherein said catalyst have different performance characteristics, or have different operating characteristics, or have different performance and operating characteristics.

* * * * *